United States Patent [19]
Broger et al.

[11] Patent Number: 5,852,212
[45] Date of Patent: *Dec. 22, 1998

[54] PROCESS FOR PREPARATION OF OPTICALLY ACTIVE α-BROMO AND α-CHLOROCARBOXYLIC COMPOUNDS

[75] Inventors: Emil Albin Broger, Magden; Richard Buchecker, Zürich; Yvo Crameri, Oberwil; Teodor Lukàc, Allschwil, all of Switzerland

[73] Assignee: Rolic AG, Zug, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 662,855

[22] Filed: Jun. 12, 1996

[30] Foreign Application Priority Data

Jun. 21, 1995 [CH] Switzerland .............................. 1820/95

[51] Int. Cl.$^6$ ................................................. C07C 53/15
[52] U.S. Cl. ............................ 562/602; 562/608; 568/17; 558/14; 558/19
[58] Field of Search ..................................... 562/602, 606, 562/608; 568/17; 558/14, 19

[56] References Cited

U.S. PATENT DOCUMENTS

| 3,878,122 | 4/1975 | Pennella . | |
|---|---|---|---|
| 5,012,002 | 4/1991 | Kumobayashi | ............................ 568/17 |

FOREIGN PATENT DOCUMENTS

| 0 272 787 | 11/1987 | European Pat. Off. . |
| 0 397 042 | 5/1990 | European Pat. Off. . |
| 5255177 | 10/1993 | Japan . |
| 95/22405 | 8/1995 | WIPO . |

OTHER PUBLICATIONS

CA:124:216257 abstr of JP07278058, Azumai, Oct. 1995.
CA:115:9316 abstract of Ferroelectic liquid crystalline polysiloxanes and possible applications in nonlinear optics, Adv. Mater., Kapitza, 1990.
Tetrahedron Letters 1992, 33, pp. 7877–7880.
Takaya et al. in J. Org. Chem. 1987 52, pgs. 3174–3176.
Abstract corresponding to EP 0 397 042.
CA 120:244118 Oct. 5, 1993 abstract to JP05255177 Saburi, Masahiko.
Aldrich Catalog 1996–1997 p. 228.

*Primary Examiner*—Gary Geist
*Assistant Examiner*—Jean F. Vollano
*Attorney, Agent, or Firm*—Bryan Cave LLP

[57] ABSTRACT

Optically active α-bromo- or α-chlorocarboxylic compounds of the formula

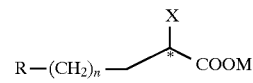

wherein
  X is bromine or chlorine;
  M is hydrogen, $NR_4^{+1}$ or a cation of an alkali or alkaline earth metal;
  $R^1$ is hydrogen or lower alkyl;
  n is 0 or 1;
  R is hydrogen, $C_1$–$C_{20}$ alkyl, or $C_1$–$C_{20}$ alkyl substituted in the terminal position with —$NR^2{}_2$, —$COOR^2$, —$OR^3$, a free or protected —CHO group or a ring A;
  $R^2$ is hydrogen or a lower alkyl;
  $R^3$ is hydrogen or a protecting group;
  ring A is an unsubstituted or substituted ring; and
  * is a center of chirality,
are prepared by enantioselectively hydrogenating, in the presence of a ruthenium complex of an optically active diphosphine ligand, a (Z)-α,β-unsaturated compound of the general formula

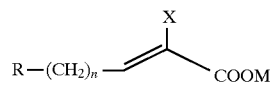

wherein R, n, X and M are as defined above.

9 Claims, No Drawings

PROCESS FOR PREPARATION OF OPTICALLY ACTIVE α-BROMO AND α-CHLOROCARBOXYLIC COMPOUNDS

FIELD OF THE INVENTION

The invention relates to a process for the manufacture of optically active α-bromo- and α-chlorocarboxylic acids and salts and esters thereof, by enantioselective hydrogenation of a corresponding α,β-unsaturated α-bromo- or α-chlorocarboxylic acid derivative in the presence of an optically active ruthenium complex.

BACKGROUND

Optically active α-bromo- and α-chlorocarboxylic acids are important and versatile intermediates for the synthesis of pharmaceutically active substances and for the synthesis of optically active liquid crystals.

Enantioselective hydrogenations of α,β-unsaturated α-fluorocarboxylic acids with ruthenium-BINAP complexes are known and are described in Tetrahedron Letters 1992, 33, 7877.

Optically active α-bromo- and α-chlorocarboxylic acids have hitherto been manufactured from optically active amino acids or α-hydroxycarboxylic acids. It has now been found that α-bromo and α-chlorocarboxylic acids can be manufactured in a simple manner and in high optical yields from the corresponding Z-α,β-unsaturated adducts by enantioselective hydrogenation.

SUMMARY OF THE INVENTION

The invention relates to a process for the preparation of an optically active α-bromo- or α-chlorocarboxylic compound of the formula

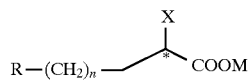

I wherein
X is bromine or chlorine;
M is hydrogen, $NR_4^{1+}$ or a cation of an alkali or alkaline earth metal;
$R^1$ is hydrogen or lower alkyl;
n is 0 or 1;
R is hydrogen, $C_1$–$C_{20}$ alkyl, or $C_1$–$C_{20}$ alkyl substituted in the terminal position with $—NR^2_2$, $—COOR^2$, $—OR^3$, a free or protected —CHO group or a ring A;
$R^2$ is hydrogen or lower alkyl;
$R^3$ is hydrogen or a protecting group;
ring A is an unsubstituted or substituted ring and;
\* is a center of chirality,
which process comprises enantioselectively hydrogenating, in the presence of a ruthenium complex of an optically active diphosphine ligand, a(Z)-α,β-unsaturated compound of the formula

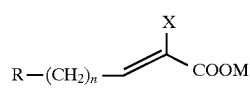

II wherein R, n, X and M are as defined above, in the presence of a ruthenium complex of an optically active. The optically active diphosphine ligand is preferably atropisomeric.

The compounds of formula I and their salts and esters are known compounds and are valuable intermediates for pharmaceutically usable end products and optically active liquid crystals. For example, amino acids, derivatives thereof or chiral dopants for liquid crystals.

DETAILED DESCRIPTION OF THE INVENTION

The term "lower alkyl" signifies a straight-chain or branched alkyl group with 1 to 5 carbon atoms such as, for example, methyl, ethyl, propyl, i-propyl, butyl, i-butyl, tert.-butyl, pentyl, i-pentyl, and the like.

The term "$C_1$–$C_{20}$ alkyl" embraces straight-chain or branched alkyl groups with 1 to 20 carbon atoms such as, for example, methyl, ethyl, propyl, butyl, pentyl, hexyl, heptyl, octyl, nonyl, decyl, isopropyl, 2-methyl-butyl, 2-methyl-pentyl, 2-methyl-hexyl, 2-methyl-heptyl, 3-methyl-butyl, 3-methyl-pentyl, 3-methyl-hexyl, 3-methyl-heptyl, 4-methyl-pentyl, 4-methyl-hexyl, 5-methyl-hexyl and the like.

Protecting groups of $R^3$ which come into consideration are the usual, readily cleavable ether-forming protecting groups for alcohols, such as, for example, benzyl, allyl, benzyloxymethyl, lower alkoxymethyl or also 2-methoxylethoxymethyl and the like.

The term "protected —CHO group" embraces, for example, acetals such as diethyl acetals, 1,3-dioxanes, 1,3-dioxolanes and the like.

The term "unsubstituted or substituted ring" embraces in connection with ring A saturated 5- or 6-membered rings which can be mono-substituted, such as, for example, cyclopentyl or cyclohexyl; or unsaturated or, respectively, aromatic 5- or 6- membered rings which can be mono-substituted, such as, for example, cyclopentene, cyclohexene, cyclohexadiene, phenyl, furan, thiophene, pyridine, pyrimidine and the like; or condensed rings such as naphthalene, tetrahydronaphthalene, indole, benzimidazole, quinoline, benzopyran and the like. Substituents which come into consideration for the aforementioned rings are, for example, lower alkyl, lower alkoxy, which can optionally carry hydroxy, $NH_2$, bromine or iodine in the terminal position, $—NR^2_2$, $—COOR^2$, $—OR^3$, a free or protected —CHO group and on aromatic rings also halogen.

The term "cation of an alkali or alkaline earth metal" embraces $Na^+$, $K^+$, $Mg^{2+}$, $Ca^{2+}$ and the like Ruthenium complexes of optically active atropisomeric diphosphine ligands which come into consideration are especially compounds of the general formulas

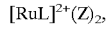  III

  IV or

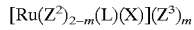  V wherein
Z is $BF_4^\ominus$, $ClO_4^\ominus$, $B(phenyl)_4^\ominus$ or $PF_6^\ominus$;
$Z^1$ is halogen or the group $Y—COO^\ominus$ or $Y—SO_3^\ominus$;
Y is lower alkyl, phenyl, halogenated lower alkyl or halogenated phenyl;
$Z^2$ is halogen;
X is benzene, hexamethylbenzene or p-cymene;
m is the number 1 or 2;
$Z^3$ is halogen, $BF_4^\ominus$, $ClO_4^\ominus$ or $B(phenyl)_4^\ominus$; and
L is an optically active, atropisomeric diphosphine ligand.

Preferred optically active atropisomeric diphosphine ligands L are compounds of the formulas

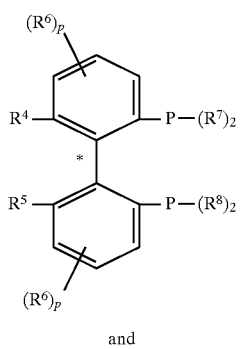

VI

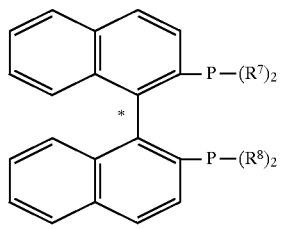

VII in the (S) or (R) form,
wherein
R$^4$ and R$^5$ each independently are lower alkyl, lower alkoxy, hydroxy or protected hydroxy or together signify —O—CH$_2$— or —O—CH$_2$—O—,
R$^6$ is lower alkyl or lower alkoxy;
p is 0, 1 or 2; and
R$^7$ and R$^8$ each independently are lower alkyl, cycloalkyl, aryl or a 5-membered heteroaromatic or together with the phosphorus atom are a group of the formula

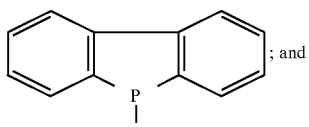

; and

* denotes a center of chirality.
Compounds of general formula VIII

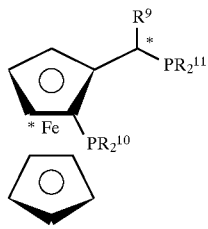

VIII wherein
R$^9$ is cycloalkyl or lower alkyl;
R$^{10}$ is aryl or heteroaryl; and
R$^{11}$ is aryl, heteroaryl or lower alkyl; and
* denotes a center of chirality,
are also suitable as optically active diphosphine ligands for the process in accordance with the invention.

The following definitions of terms apply in connection with the compounds of formulas III to VIII.

The term "lower alkyl" used in connection with formulas III–VIII has the significance defined above. The term "lower alkoxy" signifies groups in which the alkyl residue is a lower alkyl residue.

The term "halogenated lower alkyl" signifies lower alkyl groups having a variable number of halogen atoms, especially chlorine or fluorine. Preferably at least one halogen atom is situated in the α-positon to the —COO group. Preferred halogenated lower alkyl groups are perfluorinated and perchlorinated lower alkyl groups, for example trifluoromethyl, pentafluoroethyl and the like.

The term "halogenated phenyl" embraces phenyl which is mono- or multiply-substituted with fluorine, chlorine, bromine or iodine, preferably perfluorophenyl or perfluorobiphenyl.

The term "halogen" signifies fluorine, chlorine, bromine or iodine.

As protecting groups for the hydroxy groups in connection with compounds of formulae III–VIII there are used especially the usual ether-forming groups such as, for example, benzyl, allyl, benzyloxymethyl, lower alkoxymethyl or also 2-methoxyethoxymethyl and the like.

The term "cycloalkyl" denotes rings with 3–8 carbon atoms such as cyclopropyl, cyclobutyl, cyclopentyl, cyclohexyl or cycloheptyl.

The term "aryl" signifies in the scope of the present invention a phenyl, which can be not only unsubstituted but also mono-substituted in the ortho-, meta- or para-position or also multiply substituted. Suitable substituents are phenyl; lower alkyl or lower alkoxy groups, preferably methyl or methoxy groups; di-lower alkylamino, preferably dimethylamino; fluorine; trialkylsilyl such as trimethylsilyl; sulphamoyl such as N,N-dimethylamino-sulphamoyl; sulphonyl or a sulphonyl salt and the like. Moreover, the term "aryl" can also signify naphthyl.

The term "five-membered heteroaromatic" stands for a substituent of the formula

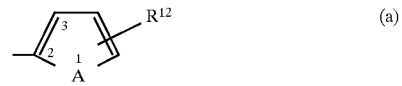

(a)

(b)

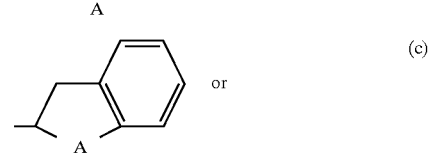

or (c)

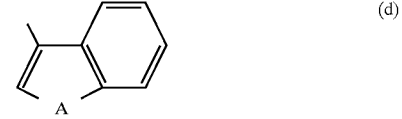

(d)

In the formulas (a) to (d), A is oxygen, sulphur or —NR$_2^{13}$, R$^{12}$ is hydrogen, lower alkyl, especially methyl, or lower alkoxy, especially methoxy, and R$^{13}$ is for lower alkyl, preferably methyl.

The symbol (*) signifies that the C atom in question is an asymmetric C atom.

The compounds of formula 11 which are used as the adduct are known compounds or analogues of known compounds which can be prepared in a known manner or readily in a manner analogous to the preparation of known compounds of formula II.

Complexes of formula IIII are known or analogues of known compounds and can be prepared in a known manner, for example as described by Takaya et al. in J. Org. Chem. 1987, 52, 3174–3177.

The complexes of formulas IV and V are also known compounds or analogues of known compounds and can be prepared, for example, as described in EP 397 042.

The diphosphine ligands of formulas VI, VII and VIII are known compounds or analogues of known compounds which can be prepared readily in a manner analogous to the preparation of the known compounds of formulas VI, VII and VIII.

The asymmetric hydrogenations of compounds of formula II to compounds of formula I are conveniently effected in an organic solvent which is inert under the reaction conditions or in water. Thus, for example, suitable solvents are lower alcohols such as methanol, ethanol, propanol and the like; halogenated hydrocarbons such as dichloromethane, chloroform, hexafluorobenzene and the like; ethers such as tetrahydrofuran, dioxan and the like; ketones such as acetone, diethyl ketone, methyl ethyl ketone; acids such as acetic acid; esters such as ethyl acetate; hydrocarbons such as pentane, hexane and the like; or mixtures of the above-mentioned solvents with one another or with water.

The ratio of ruthenium to ligand L in the complexes of formulas III, IV and V conveniently lies between about 0.5 and about 2 mol, preferably at about 1 mol, of ruthenium per mol of ligand. The substrate/catalyst ratio (S/C; mol/mol) conveniently lies between about 20 and about 30000, preferably between about 100 and about 5000.

The asymmetric hydrogenation using the complexes of formulae III, IV and V is conveniently effected at a temperature of about 10° C. to about 100° C., preferably at about 20° C. to about 60° C. This hydrogenation is conveniently effected under pressure, preferably at a pressure of about 1 to about 100 bar, especially of about 2 to about 80 bar.

The process in accordance with the invention is especially suitable for the manufacture of compounds of formula I in which R signifies hydrogen; straight-chain $C_1$–$C_{12}$ alkyl groups which are unsubstituted; and straight-chain $C_1$–$C_{12}$ alkyl groups which are substituted in the terminal position with a hydroxy group or a group of the formulas $(CH_3O)_2CH$—, $(C_2H_5O)_2CH$—, or an unsubstituted or substituted ring of the formula

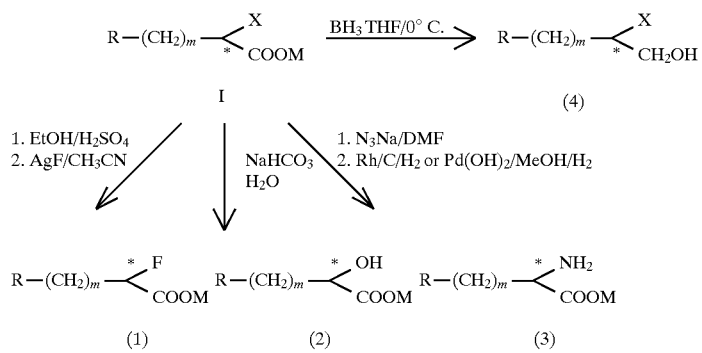

Substituents which come into consideration on the above-mentioned rings are lower alkyl or lower alkoxy groups which are unsubstituted or are substituted with hydroxy, $NH_2$, bromine or iodine in the terminal position. The 6-membered rings are preferably substituted in the 4-position, the 5-membered rings are preferably substituted in the 3-position and the condensed rings are preferably substituted in the 6-position.

The process in accordance with the invention provides access in a simple manner to a series of interesting intermediates such as, for example, optically active α-fluoro- (1), α-hydroxy- (2), α-aminocarboxylic acids (3) and alcohols (4), and respectively, salts or esters thereof, as set forth in Scheme 1.

SCHEME 1

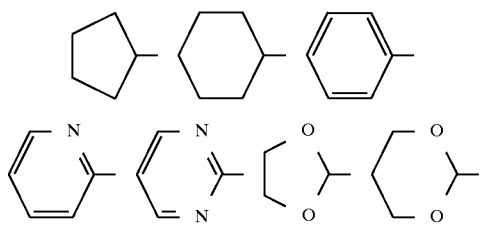

In Scheme I, m=n+1.

The conversion of compounds of formula I into the corresponding α-hydroxy derivatives (2) is effected directly from the free acid or a salt. For the conversion of compounds of formula I into the corresponding α-fluoro- (1) or α-aminocarboxylic acids (3) there is conveniently firstly formed an ester which can subsequently be cleaved without problems. The compounds of formula I can be converted into the corresponding alcohols (4) by reduction, for example with a $BH_3.THF$ complex.

As already mentioned the compounds of (1), (2), (3), and (4) are known to be useful for intermediates for the preparation of pharmaceutically active compounds or liquid crystals.

The following Examples illustrate the invention and do not represent any limitations. The abbreviations used are explained hereinafter:

| | |
|---|---|
| GC area % | gas chromatography area percent. |
| ee | enantiomeric excess |
| BIPHEMP | (6,6'-dimethylbiphenyl-2,2'-diyl)bis-(diphenylphosphine), |
| BINAP | [(1,1'-binaphthyl)-2,2'-diyl]bis(diphenyl-phosphine), |
| Cy$_2$—MeOBIPHEP | (S)—P2,P2-dicyclohexyl-6,6'-dimethoxy-P2',P2'-diphenyl-biphenyl-2,2'-bis-phosphine, |
| 2-Furyl$_2$-BIPHEMP | P,P-diphenyl-P',P,-di-2-furylphenyl)-(6,6'-dimethyl-biphenyl-2,2'-diyl)diphosphine, |
| Cy$_4$—MeOBIPHEP | (6,6'-dimethoxylbiphenyl-2,2'-diyl)bis-(dicyclohexyl-phosphine), |
| (S)-(3,5-Ipr,4-MeO)—MeOBIPHEP | (S)-6,6'-dimethyl-P,P,P',P'-tetrakis-(diisopropyl-4-methoxy-phenyl)-biphenyl- |

-continued

| | |
|---|---|
| Ipr$_4$—MeOBIPHEP | 2,2'-bis phosphine, (6,6'-dimethoxylbiphenyl-2,2'-diyl)bis-(diisopropyll-phosphine), |
| (R)—(S)—PPF—P(tBu)$_2$ | {(R)-1-[(S)-2-(diphenylphosphino)ferrocenyl]}ethyl-di-tert.-butylphosphine, |
| MePHOS—MeOBIPHEP | [{2,5-dimethyl-phospholan-1-yl}-6,6'-dimethoxy-biphenyl-2-yl]-2,5-dimethyl-phospholane, |
| MeOBIPHEP—TS—Na | 6,6'-dimethoxybiphenyl-2,2'-bis(4,4'-phosphin-diyl-dibenzenesulphonic acid sodium salt |

EXAMPLE 1

7.4 mg (0.0226 mmol) of bis($\eta^2$-acetato)($\eta^4$-cycloocta-1,5-diene)ruthenium(II) and 12.5 mg (0.0226 mmol) of (R)-BIPHEMP were dissolved in a mixture of 6 ml of diethyl ether and 2 ml of tetrahydrofuran in a glove box (O$_2$ content <1 ppm) and stirred at 40° for 1.5 hours. Then, 0.5 g (2.26 mmol) of (Z)-2-bromo-2-octenoic acid and 60 ml of methanol were placed in a 185 ml autoclave in the glove box and the above-prepared catalyst solution was added. The autoclave was sealed and the hydrogenation was carried out at 20° while stirring and under a constant pressure of 50 bar. The hydrogenation was interrupted after 17 hours. The conversion was 93%. The hydrogenation solution was evaporated at 50°/20 mbar and the residue was distilled at 115°/0.2 mbar in a bulb tube oven. 0.4 g (80%) of a mixture comprising 93% (R)-2-bromo-octanoic acid (94.3% ee) and 7% adduct was obtained as a colourless oil. For the ee determination, a sample of the product was esterified with diazomethane and analyzed by gas chromatography on a chiral phase (permethylated-cyclodextrin mixed with OV-61).

EXAMPLE 2

A catalyst solution was prepared by dissolving 0.35 g (0.45 mmol) of Ru(OAc)$_2$[(R)-BIPHEMP] in 20 ml of methanol in a glove box (O$_2$ content <1 ppm) and was stirred at 20° for 15 min. Then, 10.0 g (45.2 mmol) of (Z)-2-bromo-2-octenoic acid and 94 ml of methanol were placed in a 185 ml autoclave and the above-prepared catalyst solution was added. The autoclave was sealed and the hydrogenation was carried out at 20° while stirring and under a constant pressure of 50 bar. After 3 hours the conversion was 100%. The hydrogenation solution was evaporated at 50°/20 mbar and the residue was distilled at 115°/0.2 mbar in a bulb tube oven. 9.4 g (94%) of a mixture comprising 98.6% (R)-2-bromo-octanoic acid (93.8% ee) and 1.4% adduct were obtained as a colourless oil.

EXAMPLE 3

A catalyst solution was prepared by dissolving 59.6 mg (0.045 mmol) of Ru(CF$_3$COO)$_2$[(S)-MeOBIPHEP-TS-Na] in 20 ml of water in a glove box (O$_2$ content <1 ppm) and was stirred at 20° for 15 min. Then, 1.0 g (4.52 mmol) of (Z)-2-bromo-2-octenoic acid, 30 ml of water and 0.46 g (4.52 mmol) of triethylamine were placed in a 185 ml autoclave and the above-prepared 20 ml of catalyst solution were added. The autoclave was sealed and the hydrogenation was carried out at 20° while stirring and under a constant pressure of 50 bar. After 4 hours the conversion was 100%. The hydrogenation solution was acidified to pH 1 with 1N HCl solution and extracted with diethyl ether. After drying and evaporating the ether extract (40°/20 mbar) the residue was distilled at 115°/0.2 mbar in a bulb tube oven. There was obtained 0.9 g (90%) of (S)-2-bromo-octanoic acid as a colourless oil; chem. purity 98.9 GC area %; 93.0% ee.

EXAMPLES 4–26

The hydrogenations set forth in Table 1 were carried out in a manner analogous to Example 1 or 2.

TABLE 1

Asymmetric hydrogenation of 2-bromo- and 2-chloro-2-alkenoic acids (R—CH=CXCOOM)

| Ex. | Conf. | X | R | M | T °C. | Pres. bar | Ligand L[1] | % Conv. 20 h | % ee |
|---|---|---|---|---|---|---|---|---|---|
| 4 | Z | Cl | n-C$_5$H$_{11}$ | H | 20 | 50 | (R)-BIPHEMP | 100 | 91.2 (R) |
| 5 | Z | Cl | n-C$_5$H$_{11}$ | H | 20 | 50 | (S)-BINAP | 97 | 76.3 (S) |
| 6 | Z | Br | n-C$_4$H$_9$ | H | 20 | 50 | (R)-BIPHEMP | 100 | 94.1 (R) |
| 7 | Z | Br | n-C$_6$H$_{13}$ | H | 20 | 50 | (R)-BIPHEMP | 100 | 94.4 (R) |
| 8 | Z | Br | n-C$_6$H$_{13}$ | H | 20 | 50 | (R)-Cy$_2$-MeOBIPHEP | 1.00 | 77.3 (R) |
| 9 | Z | Br | n-C$_6$H$_{13}$ | H | 20 | 50 | (R)-2-Furyl$_2$-BIPHEMP | 100 | 78.0 (R) |
| 10 | Z | Br | n-C$_5$H$_{11}$ | H | 20 | 50 | (S)-(3,5-lpr,4-MeO)-MeOBIPHEP | 100 | 78.9 (S) |
| 11 | Z | Br | n-C$_5$H$_{11}$ | H | 20 | 50 | (R,R,R)-MePHOS-MeOBIPHEP[3] | 24 | 78.6 (R) |
| 12 | Z | Br | n-C$_5$H$_{11}$ | H | 20 | 50 | (R)-Ipr$_4$-MeOBIPHEP | 69 | 84.8 (R) |
| 13 | Z | Br | n-C$_5$H$_{11}$ | H | 20 | 50 | (R)-Cy$_4$-MeOBIPHEP | 100 | 88.3 (R) |
| 14 | Z | Br | n-C$_5$H$_{11}$ | H | 20 | 50 | (R)-(S)-PPF-P(tBu)$_2$[2] | 98 | 84.4 (R) |
| 15 | Z | Br | n-C$_3$H$_7$ | H | 20 | 50 | (R)-BIPHEMP | 99 | 92.1 (R) |
| 16 | Z | Br | n-C$_7$H$_{15}$ | H | 20 | 50 | (R)-BIPHEMP | 100 | 93.6 (R) |
| 17 | Z | Br | n-C$_8$H$_{17}$ | H | 20 | 50 | (S)-BIPHEMP | 100 | 93.5 (S) |
| 18 | Z | Br | n-C$_5$H$_{11}$ | NH$_4^+$ | 20 | 50 | (R)-BIPHEMP | 100 | 90.7 (R) |
| 19 | Z | Br | n-C$_5$H$_{11}$ | Et$_3$NH$^+$ | 20 | 50 | (R)-BIPHEMP | 100 | 87.3 (R) |
| 20 | E | Cl | n-C$_5$H$_{11}$ | H | 20 | 50 | (R)-BIPHEMP | 100 | 10.1 (R) |
| 21 | E | Cl | n-C$_5$H$_{11}$ | H | 20 | 50 | (S)-BINAP | 100 | 9.0 (S) |
| 22 | E | Br | n-C$_4$H$_9$ | H | 20 | 50 | (R)-BIPHEMP | 100 | 4.1 (S) |

TABLE 1-continued

Asymmetric hydrogenation of 2-bromo- and 2-chloro-2-alkenoic acids (R—CH=CXCOOM)

| Ex. | Conf. | X | R | M | T °C. | Pres. bar | Ligand L[1] | % Conv. 20 h | % ee |
|---|---|---|---|---|---|---|---|---|---|
| 23 | Z | Br | n-$C_5H_{11}$ | H | 50 | 50 | (R)-BIPHEMP | 100 | 93.3 (R) |
| 24 | Z | Br | n-$C_5H_{11}$ | H | 100 | 50 | (S)-BIPHEMP | 100 | 63.8 (S) |
| 25 | Z | Br | n-$C_5H_{11}$ | H | 20 | 100 | (S)-BIPHEMP | 100 | 91.6 (S) |
| 26 | Z | Br | n-$C_5H_{11}$ | H | 20 | 10 | (S)-BIPHEMP | 100 | 91.2 (S) |

[1])Catalyst preparation: analogous to Example 2
[2])Catalyst preparation: analogous to Example 1
[3])Prepared according to M. Scalone, Abstract at the 9th International Symposium on Homogeneous Catalysis, Jerusalem, August 21–26, 1994.

EXAMPLE 27

A catalyst solution was prepared by dissolving 0.035 g (0.0045 mmol) of Ru(OAc)$_2$[(R)-BIPHEMP] and 17.2 mg (0.0905 mmol) of an 85 percent ethereal HBF$_4$ solution in 20 ml of methanol in a glove box (O$_2$ content <1 ppm) and was stirred at 20° for 1.5 hours. Then, 1.0 g (4.52 mmol) of (Z)-2-bromo-2-octenoic acid and 105 ml of methanol were placed in a 185 ml autoclave and the above-prepared catalyst solution was added. The autoclave was sealed and the hydrogenation was carried out at 50° while stirring and under a constant pressure of 50 bar. After 21 hours the conversion was 98%. The hydrogenation solution was evaporated at 50°/20 mbar and the residue was distilled at 115°/0.2 mbar in a bulb tube oven. There was obtained 0.6 g of (R)-2-bromo-octanoic acid as a colourless oil; chem. purity 97.3 GC area%; 86.0% ee.

EXAMPLE 28

A catalyst solution was prepared by dissolving 0.035 g (0.045 mmol) of Ru(OAc)$_2$[(R)-BIPHEMP] and 1 ml of a 0.09 molar methanolic HCl solution in 20 ml of methanol in a glove box (O$_2$ content <1 ppm) and was stirred at 20° for 1.5 hours. Then, 1.0 g (4.52 mmol) of (Z)-2-bromo-2-octenoic acid and 105 ml of methanol were placed in a 185 ml autoclave and the above-prepared catalyst solution was added. The autoclave was sealed and the hydrogenation was carried out at 50° while stirring and under a constant pressure of 50 bar. After 21 hours the conversion was 87%. The hydrogenation solution was evaporated at 50°/20 mbar and the residue was distilled at 115°/0.2 mbar in a bulb tube oven. There was obtained 0.6 g of a mixture comprising 86% (R)-2-bromo-octanoic acid (85.4% ee) and 14% adduct as a colourless oil.

We claim:

1. A process for the preparation of an optically active α-bromo- or α-chlorocarboxylic compound of the formula

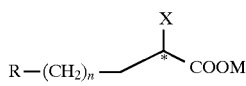

wherein

X is bromine or chlorine;

M is hydrogen, NR$_4^{+1}$ or a cation of an alkali or alkaline earth metal;

R$^1$ is hydrogen or lower alkyl;

n is 0 or 1;

R is hydrogen, $C_1$–$C_{20}$ alkyl, or $C_1$–$C_{20}$ alkyl substituted in the terminal position with —NR$^2{}_2$, —COOR$^2$, —OR$^3$, a free or protected —CHO group or a ring A;

R$^2$ is hydrogen or a lower alkyl;

R$^3$ is hydrogen or a protecting group;

ring A is an unsubstituted or substituted ring; and

* is a center of chirality, which process comprises enantioselectively hydrogenating, in the presence of a ruthenium complex of an optically active diphosphine ligand, a (Z)-α,β-unsaturated compound of the general formula

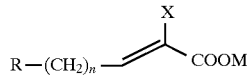

wherein R, n, X and M are as defined above.

2. A process according to claim 1, wherein the ruthenium complex is selected from compounds of the formulas

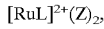      III

      IV or

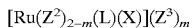      V wherein

Z is $BF_4^\ominus$, $ClO_4^\ominus$, B(phenyl)$_4^\ominus$ or $PF_6^\ominus$;

Z$^1$ is halogen or the group Y—COO$^\ominus$ or Y—SO$_3^\ominus$;

Y is lower alkyl, phenyl, halogenated lower alkyl or halogenated phenyl;

Z2 is halogen;

X is benzene, hexamethylbenzene or p-cymene;

m is the number 1 or 2;

Z$^3$ is halogen, $BF_4^\ominus$, $ClO_4^\ominus$ or B(phenyl)$_4^\ominus$; and

L is an optically active, atropisomeric diphosphine ligand.

3. A process according to claim 2, wherein the atropisomeric ligand L is a compound of the formula

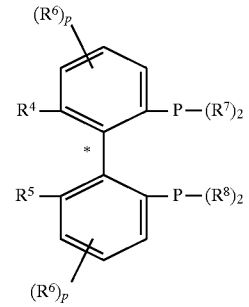

-continued
or

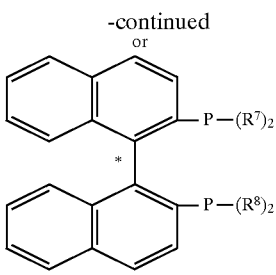

in the (S) or (R) form,
wherein
R⁴ and R⁵ each independently are lower alkyl, lower alkoxy, hydroxy or protected hydroxy or together signify —O—CH₂— or —O—CH₂—O—,
R⁶ is lower alkyl or lower alkoxy;
p is 0, 1 or 2; and
R⁷ and R⁸ each independently are lower alkyl, cycloalkyl, aryl or a 5-membered heteroaromatic or together with the phosphorus atom are a group of the formula

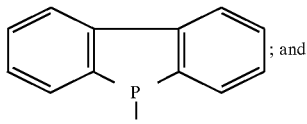

\* denotes a centre of chirality.

4. A process according to claim 2, wherein the atropisomeric ligand L is a compound of the formula

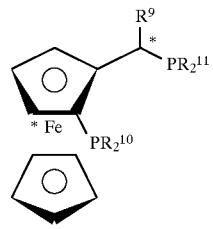

wherein

R⁹ is cycloalkyl or lower alkyl;

R¹⁰ is aryl or heteroaryl; and

R¹¹ is aryl, heteroaryl or lower alkyl; and

\* denotes a centre of chirality.

5. A process according to claim 2, wherein the ratio of ruthenium to ligand L is from about 0.5 to about 2 mol.

6. A process according to claim 2, having a substrate/catalyst ratio (S/C; mol/mol) of from about 20 to about 30000.

7. A process according to claim 2, wherein the enantioselective hydrogenation of a compound of formula II is carried out at a temperature of about 20° C. to about 60° C. and a pressure of about 2 to about 80 bar.

8. A process according to claim 1, wherein R is hydrogen, a straight-chain C₁–C₁₂ alkyl group which is unsubstituted, or a straight-chain C₁–C₁₂ alkyl group which is substituted in the terminal position with a hydroxy group, (CH₃O)₂CH—, (C₂H₅O)₂CH— or an unsubstituted or substituted ring of one of the formulas

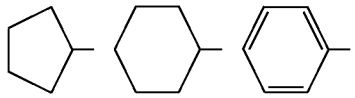

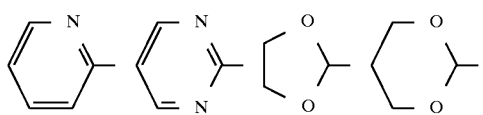

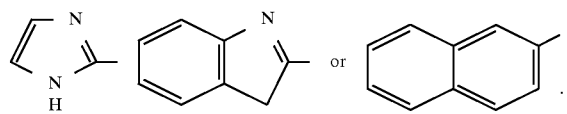

9. A process according to claim 8, wherein X is bromine, M is hydrogen, and R is propyl.

\* \* \* \* \*

UNITED STATES PATENT AND TRADEMARK OFFICE
CERTIFICATE OF CORRECTION

PATENT NO. : 5,852,212
DATED : December 22, 1998
INVENTOR(S) : Emil Albin Broger, et al.

BEST AVAILABLE COPY

It is certified that error appears in the above-identified patent and that said Letters Patent is hereby corrected as shown below:

In line 12 of claim 2 (column 10, line 46), "Z2" should be changed to $--Z^2--$.

Signed and Sealed this

Twenty-fifth Day of May, 1999

Attest:

Q. TODD DICKINSON

*Attesting Officer*    *Acting Commissioner of Patents and Trademarks*